(12) United States Patent
Tegg et al.

(10) Patent No.: US 8,577,447 B2
(45) Date of Patent: Nov. 5, 2013

(54) OPTIC-BASED CONTACT SENSING ASSEMBLY AND SYSTEM

(75) Inventors: Troy T. Tegg, Elk River, MN (US); Saurav Paul, Minnetonka, MN (US); Richard E. Stehr, Stillwater, MN (US); Reed R. Heimbecher, Hamel, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 979 days.

(21) Appl. No.: 11/941,073

(22) Filed: Nov. 15, 2007

(65) Prior Publication Data

US 2008/0275428 A1 Nov. 6, 2008

Related U.S. Application Data

(60) Provisional application No. 60/915,387, filed on May 1, 2007.

(51) Int. Cl.
*A61B 18/14* (2006.01)

(52) U.S. Cl.
USPC ............................ 600/476; 606/41; 385/13

(58) Field of Classification Search
None
See application file for complete search history.

(56) References Cited

U.S. PATENT DOCUMENTS

| | | | | |
|---|---|---|---|---|
| 4,757,194 A * | 7/1988 | Simms | ............... | 250/227.21 |
| 4,834,101 A | 5/1989 | Collison et al. | | |
| 5,122,137 A * | 6/1992 | Lennox | ............... | 606/40 |
| 5,413,107 A | 5/1995 | Oakley et al. | | |
| 5,460,182 A | 10/1995 | Goodman et al. | | |
| 5,928,222 A | 7/1999 | Kleinerman | | |
| 6,113,590 A * | 9/2000 | Fischer et al. | ............... | 606/28 |
| 6,743,239 B1 | 6/2004 | Kuehn et al. | | |
| 7,060,965 B2 | 6/2006 | Vidovic et al. | | |
| 8,048,063 B2 | 11/2011 | Aeby et al. | | |
| 2002/0123749 A1 | 9/2002 | Jain | | |
| 2004/0116992 A1 | 6/2004 | Wardle et al. | | |
| 2005/0245789 A1 | 11/2005 | Smith et al. | | |
| 2007/0060847 A1 | 3/2007 | Leo et al. | | |
| 2008/0009750 A1 | 1/2008 | Aeby et al. | | |
| 2009/0060977 A1 | 3/2009 | Lamson et al. | | |
| 2009/0093806 A1 | 4/2009 | Govari et al. | | |
| 2009/0131931 A1 | 5/2009 | Lee et al. | | |

FOREIGN PATENT DOCUMENTS

| | | |
|---|---|---|
| EP | 0900549 | 3/1999 |
| EP | 2 062 545 A2 | 5/2009 |
| WO | WO-2004/069072 | 8/2004 |

OTHER PUBLICATIONS

International Search Report and Written Opinion for PCT/US2008/061092 mailed Sep. 3, 2008.
"High-Tech Partnership Bundles Catheters With Fiber-Optic Sensors," p. 6, Medical Product Manufacturing News, Sep. 2007.
Bioseb: Samba—Blood Pressure System, http://www.bioseb.com/bioseb/anglais/default/item id=904 cat id=3 Samba%20Blood%20Pressure%20System.php, Oct. 15, 2007.

(Continued)

*Primary Examiner* — Jacqueline Cheng
(74) *Attorney, Agent, or Firm* — Dykema Gossett PLLC

(57) ABSTRACT

The invention relates to an optic-based sensing assembly and a system incorporating the assembly and related use of the assembly. In particular, the invention relates to an optic-based catheter assembly and related system used to determine contact between a catheter and surrounding proximate environment, such as tissue. An embodiment of such a system may, for example, be used for visualization, mapping, ablation, or other methods of diagnosis and treatment of tissue and/or surrounding areas.

22 Claims, 13 Drawing Sheets

(56) References Cited

OTHER PUBLICATIONS

Samba Sensors —The Samba Technology, http://www.samba.se/index2.cfm?PageID=45, Oct. 15, 2007.
Publications Related to Samba Sensors AB
Micro Pressure Measurement System, Product Overview, Samba 200 Control Unit and Samba Preclin Pressure Transducer, Samba Sensors.
Interferometer Fabry-Perot, Fiber Optic Interferometer Fabry-Perot, http://physics.nad.ru/Physics/English/ifp_txt.htm, Oct. 15, 2007.
J. Peirs et al., "Design of an Optical Force Sensor for Force Feedback During Minimally Invasive Robotic Surgery," http://www.mech.kuleuven.ac.be.
"International Search Report & Written Opinion", PCT/US2009/069857 Mar. 2, 2010.
"Supplementary European Search Report", EP 08746501 Jul. 2, 2012.

* cited by examiner

OPTIC-BASED CONTACT SENSING ASSEMBLY AND SYSTEM

CROSS-REFERENCE TO RELATED APPLICATIONS

This application claims the benefit of U.S. provisional application No. 60/915,387, filed 1 May 2007, which is hereby incorporated by reference as though fully set forth herein.

BACKGROUND OF THE INVENTION a. Field of the Invention

The instant invention relates to an optic-based sensing assembly. The instant invention includes an optic-based catheter assembly and related system used to monitor or determine contact between a catheter and the surrounding proximate environment, such as tissue. Such a system may be used for visualization, mapping, ablation, and/or other methods of diagnosis and treatment of tissue.

b. Background Art

The visualization and treatment of organs and tissues has been advanced through the increasing use of catheter systems. Catheter systems have been designed for the incorporation of various components to treat and diagnose ailments, as accomplished through the mapping of organs, sensing of thermal and electrical changes exhibited by a tissue (e.g., heart), as well as the application of energizing sources (such as radiofrequency, cryogenics, laser, and high frequency ultrasound) to tissue.

Catheter systems generally include a portion that contacts the tissue or organ, or is inserted in an environment (e.g., heart chamber or vessel) to detect a number of parameters, such as for example, location of the tissue, contact or pressure exerted on the tissue, electrophysiological attributes of the tissue, or other type of parameters that aid in the evaluation or treatment of the organ or tissue.

It is known that sufficient contact between a catheter, in particular an electrode provided in connection with a catheter, and tissue during a procedure is generally necessary to ensure that the procedures are effective and safe. Current techniques of mapping, visualization and treatment using energizing sources, such as the use of radiofrequency energy during ablation, rely on the placing of the electrode of a catheter system in consistent mechanical contact with targeted tissue. Perforations of the cardiac wall as well as lesion formation (such as lesions created by exposure to radiofrequency) partially depends upon the direction of contact between the electrode and tissue. In particular, for endocardial catheter applications, the point of electrode-tissue contact is typically 150 cm away from the point of application of force applied by the operator (whether manual or automated) of the catheter outside of the body. Coupled with the fact that a beating heart is a dynamically moving wall, this gives rise to some functional and theoretical challenges such as ensuring that the electrode is in sufficiently constant mechanical contact with the myocardial wall.

Catheter systems having sensor assemblies, such as those mounted on the catheter shaft proximal to the electrode or remotely in the handle set, leave the possibility, however small, of obtaining false positive outcomes when detecting contact between the electrode and the tissue. False positive outcomes may occur, for example, when the catheter wall, and not the electrode, is in contact with the tissue. Such condition may arise during the catheter manipulation in the heart when, for instance, the distal portion of the catheter is curled inward so much as to lose electrode contact with the tissue, while the distal portion of the catheter is in contact with the tissue. When that happens, remotely placed sensors generate signals due to the deflection of the catheter shaft, thereby falsely indicating contact between the electrode and tissue. Accordingly, optic-based contact sensors coupled to the electrode can, among other things, help reduce the possibility of obtaining false positive outcomes when detecting contact between the electrode and the tissue.

BRIEF SUMMARY OF INVENTION

For some applications, it is desirable to have an optic-based catheter system that includes an optical sensor that detects changes in reflected energy, such as light, from an optically interactive surface provided by an electrode. In an embodiment, the electrode is subjected to a compressive force due to mechanical contact of the electrode surface with another body or surface. The optical sensor of the present invention can be used to measure contact of an electrode with a dynamically moving wall, such as a beating heart.

In another embodiment, a contact sensing assembly for sensing contact with a target (e.g., a tissue or other organ surface) is provided. The assembly includes an elongated body having a distal section and a sensor connected to the distal section. The sensor including a segment with a first interactive component, a tip positioned distally from the segment, and a flexible coupling member separating the segment from the tip. The tip includes an external surface and is positioned distally from the segment, the tip further including a second interactive component that is adapted to interact with the first interactive component. The flexible coupling member separates the segment from the tip, such that the second interactive component can move relative to the first interactive component when the external surface of the tip contacts the target.

Accordingly, the present invention is directed to a contact sensing assembly for detecting and measuring contact force. The inventive assembly includes a catheter having a proximal end and distal end. In an embodiment, the inventive assembly further includes an electrode having a tip portion and a base portion. The electrode further includes an optically interactive surface. A portion of the electrode may be connected to the distal end of the catheter. The inventive assembly may further provide at least one optical sensor within the catheter for interacting with the optically interactive surface provided in connection with the electrode.

The present invention is further directed to an optic-based catheter system. The inventive system includes a catheter having a proximal end and distal end. The system may further provide an electrode having a tip portion and a base portion wherein the electrode further includes an optically interactive surface and at least a portion of the electrode is connected to the distal end of the catheter. In an embodiment, the system still further may include at least one optical sensor provided within the catheter for interacting with the optically interactive surface provided by the electrode. The system may further include a light source, a processor, a catheter mapping unit for use in mapping and/or visualizing the catheter location; and a fiber assembly for carrying optical energy, such as light, emitted and received from the optical sensor.

The present invention is further directed to a method of sensing contact force as provided by the contact sensing assembly and system. The inventive method includes directing optical energy from a source through an optic fiber assembly within a catheter. In an embodiment, the inventive method may further include emitting the optical signal and/or energy from an optical sensor across a spaced gap and/or into a refractive medium for interacting with an optical interactive surface provided by an electrode. In an embodiment, the inventive method includes receiving reflected optic energy by the optical sensor, the reflected optic energy may be transmitted along the fiber assembly and processed by a processor to determine a change between the optical energy (i.e., signal) emitted from the optical sensor and the reflected optical energy received by the optical sensor to calculate or determine the corresponding force vector exerted by the electrode on a tissue. More particularly, the change in reflective energy, for example, the change in optical intensity, is proportional to the displacement or movement of the optically interactive surface of the electrode. The change in reflective energy is therein proportional to the force exerted on the electrode either axially, laterally or a combination of both.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
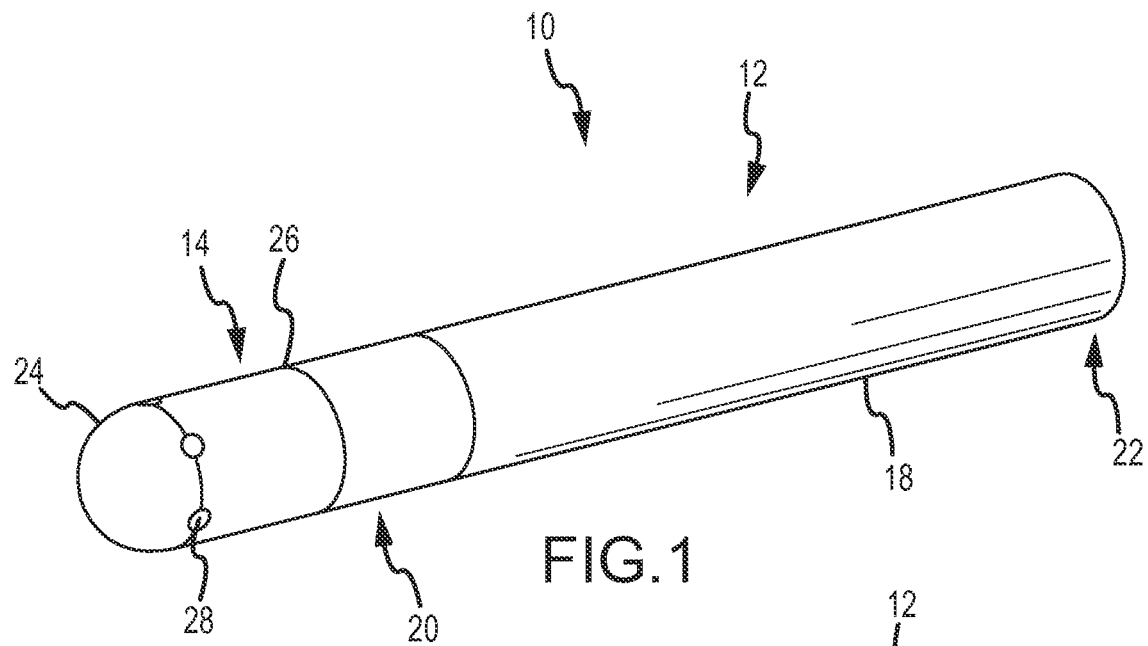
FIG. 1 is a partial perspective view of a catheter assembly in accordance with an embodiment of the present invention.
Figure 2:
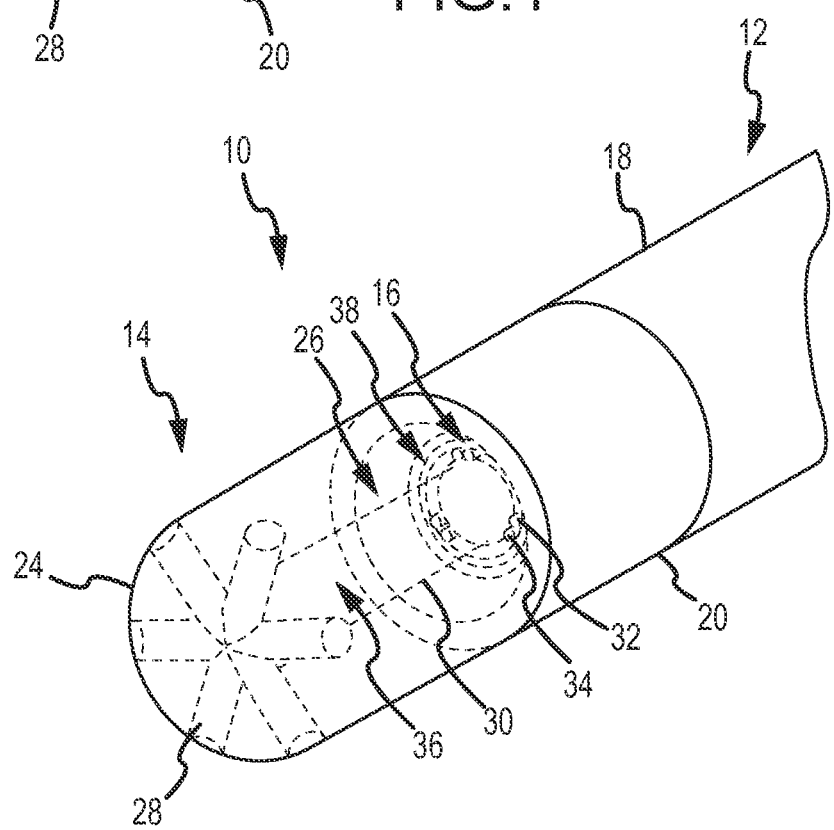
FIG. 2 is an enlarged partial perspective view of the catheter assembly shown in FIG. 1, wherein the electrode and portion of the optic-based sensing assembly is shown in phantom.

Referring now to the drawings wherein like reference numerals are used to identify like components in the various views, FIGS. 1 and 2 illustrate an exemplary embodiment of a contact sensing assembly 10 as provided by the present invention. In a general form, the contact sensing assembly 10 includes a catheter 12, an electrode 14 connected to the catheter, and an optical sensor 16 for optically interacting with a portion of electrode 14. In another embodiment, the contact sensing assembly 10 may include a first interactive component and a second interactive component. The contact sensing assembly may be used in the diagnosis, visualization, and/or treatment of tissue (such as endocardial tissue) in a body. Contact sensing assembly 10 may be used in a number of diagnostic and therapeutic applications, such as for example, the recording of electrograms in the heart, the performance of cardiac ablation procedures, and/or various other applications. The catheter assembly can be used in connection with a number of applications that involve humans, or other mammals, for tissue observation, treatment, repair or other procedures. Moreover, the present invention is not limited to one particular application, but rather may be employed by those of ordinary skill in the art in any number of diagnostic and therapeutic applications.

Catheter 12 of the present invention includes a body 18 having a distal end 20 and a proximal end 22. Body 18 of catheter 12 is generally tubular in shape, although other configurations of the catheter may be used as known in the industry. Distal end 20 of catheter 12 is connected to electrode 14, while body 18 of catheter 12 may house optical sensor 16 and may house other components used in the diagnosis and/or treatment of tissue. If desired, the outer portion of catheter 12 may have a braided outer covering therein providing increased flexibility and strength. The catheter of the present invention vary in length and are attached to a handle or other type of control member that allows a surgeon or operator of the catheter to manipulate the relative position of the catheter within the body from a remote location, as recognized by one of ordinary skill in the art.

As generally shown in FIG. 1, an embodiment of the present invention includes distal end 20 of catheter 12 that includes at least a portion or segment that exhibits increased flexibility relative to more proximal portions of the catheter 12. The increased flexibility of at least a portion or segment associated with the distal end 20 may be achieved through any number of methods, including but not limited to, the use of flexible materials, the formation of a spring-like coupling portion, or any other type of connection that allows for increased flexibility at a portion or segment of the distal end 20 of catheter 12.

Electrode 14 is connected to distal end 20 of catheter 12. Upon the exertion of external contact force on the surface of electrode 14, at least a portion of distal end 20 of catheter 12 flexes and/or bends relative to electrode 14. The relative movement (e.g., displacement either axially, laterally or a combination thereof) of distal end 20 may be proportionate or correlated to the force exerted on electrode 14. Electrode 14 includes a tip portion 24 and a base portion 26. Electrode 14 may be configured to include a means for irrigating. For example, without limitation, the incorporation of at least one irrigation port 28 within electrode 14, therein providing an irrigated electrode tip. An irrigated electrode tip allows for the cooling of electrode 14, for instance, through the transporting of fluid through electrode 14 and around the surface of the tissue. A number of different types of electrodes, irrigated and non-irrigated, may be connected and incorporated for use an electrode 14 according to embodiments of the invention depending on the type of procedures being done. Such irrigated electrodes include, but are not limited to, those disclosed in U.S. patent application Ser. No. 11/434,220 (filed May 16, 2006), Ser. No. 10/595,608 (filed Apr. 28, 2006), Ser. No. 11/646,270 (filed Dec. 28, 2006) Ser. No. 11/647,346 (filed Dec. 29, 2006) and 60/828,955 (filed Oct. 10, 2006), each of which is hereby incorporated by reference as though fully set forth herein.

Electrode 14 may include an optically interactive surface 30 (see, e.g., FIG. 5B), described further below, that is provided on a portion of the electrode 14 that interacts with the optical sensor 16 of the assembly 10. As shown in FIG. 2, electrode 14 may further include an electrode cavity 36, as shown in phantom. Electrode cavity 36 may also be used to provide a number of different components and/or functions in connection with the electrode. In one embodiment, electrode cavity 36 may further provide the optically interactive surface therein enabling optical sensor 16 to interact with the internal surface of electrode 14 provided by electrode cavity 36. In alternate embodiments, electrode cavity 36 may serve as a lumen for transferring of irrigation channels, electrical components, or any other type assembly components that need to be transferred through electrode 14.

In general, an optically interactive surface 30 may be provided on or in connection with a surface associated with electrode 14, such that the surface positioning, configuration, and orientation of the interactive surface (which has a know position with respect to the electrode) allows sufficient interaction and/or functional communication with the optical sensor 16 such that a change in the communication (e.g., optical signal, light intensity) can provide a means for determining the contact force and/or orientation of the electrode with the tissue or surrounding area. In one embodiment, electrode cavity 36 includes an optically interactive surface 30. In an alternate embodiment, optically interactive surface 30 may be provided on or in connection with base portion 26 of electrode 14. The optically interactive surface may be comprised of any material suitable for the intended environment that reflects or refracts light energy. For example, without limitation, the interactive surface may comprise a reflective metal, such as a polished metal. The interactive surface 30 may also comprise prisms or other refractive media which may include a reflective surface. Depending on the design of optically interactive surface 30, the interactive surface 30 may further include a mirrored surface, filters positioned relative to surface 30 and/or other types of refractive media in combination with opaque segments, as discussed in more detail below. Optical sensor 16 may be positioned within the distal end 20 of the catheter 12. Optical sensor 16 may include at least one optic fiber that transmits and receives an optical signal, such as light energy. The optical sensor may also be manufactured to transmit and/or receive various types of signals including those associated with electromagnetic radiation, lasers, x-rays, radiofrequency, etc. In an embodiment, optical sensor 16 may use light energy to determine the relative contact (e.g., force, stress, and/or orientation) between electrode 14 and an external surface in operational contact with the electrode—for example, tissues and surrounding environments, including organs, heart chambers, and interior of vessels. In an embodiment, the optical sensor may be adapted to measure one or more parameters, including, for example, intensity, wavelength, phase, spectrum, speed, optical path, interference, transmission, absorption, reflection, refraction, diffraction, polarization, and scattering.

In an embodiment, one or more force vectors may be used to determine the contact force and/or orientation of the electrode in connection with the surrounding tissue or other external surfaces. In particular, the change of intensity of the optical signal received by optical sensor 16 may be correlated to the contact force exerted on electrode 14 by an external surface. The intensity of the optical signals received by optical sensor 16 is proportional to the structural displacement of distal end 20 of catheter 12. As discussed in more detail below, the displacement of distal end 20 is governed by a factor (k) (such as a spring constant) exhibited by the material comprising a portion of distal end 20. Accordingly, the factor (k) may be equated to the external force (F), either laterally or axially, exerted on electrode 14, divided by the unit displacement (D) (either axially or laterally) of electrode, which may be generally expressed as k=F/D. Since the change in intensity to the optical signals is proportional to the displacement of the electrode, the external force exerted on the electrode may be determined.

Figure 3A:
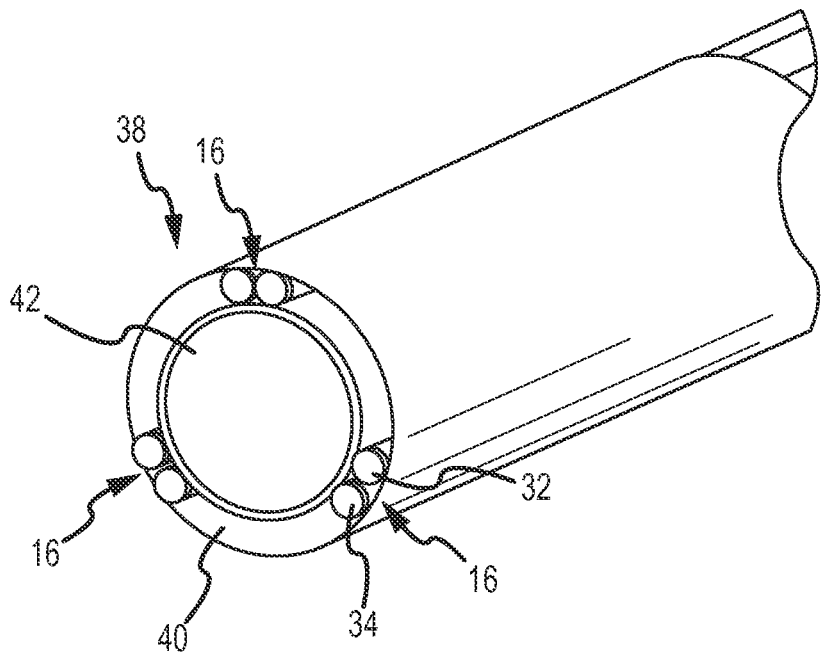
FIGS. 3A and 3B are partial perspective views of portions of an optic-based sensing assembly according to alternative embodiments of the present invention.
Figure 3B:
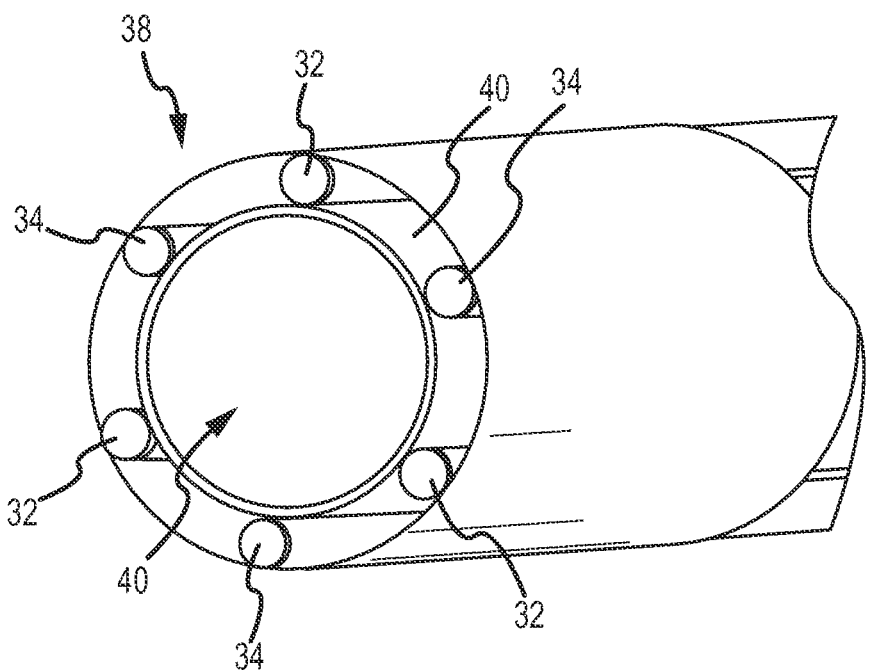
Figure 4:
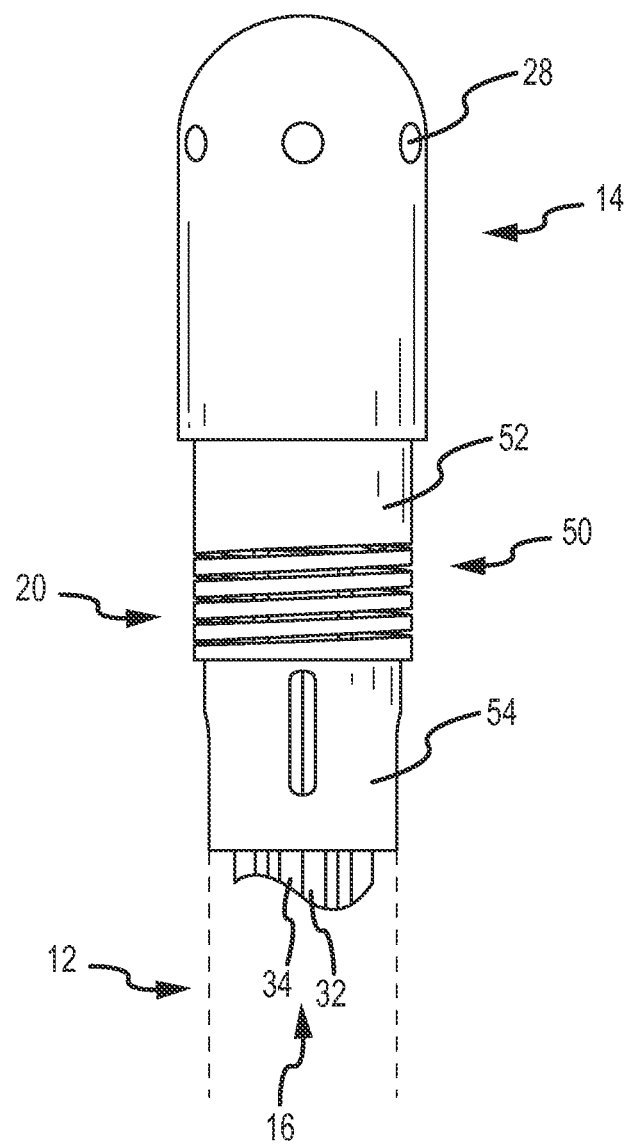
FIG. 4 is a side elevation view of an alternate embodiment of the present invention.

In order to determine light or optical intensity, optical sensor 16 includes a receiver 32 and an emitter 34 for receiving and emitting light energy, respectively. Receiver 32 and emitter 34 may be included in a single fiber optic cable or in two separate fiber optic cables, such as shown in FIG. 2. A number of optical sensors 16 may be arranged within distal end 20 of catheter 12 to operatively (e.g., optically) interact with an interactive surface 30 that is provided in connection with electrode 14. Moreover, a number of receivers 32 and emitters 34 may be disposed within distal end 20 of catheter 12 in various configurations and combinations to assess contact and/or orientation readings. Such positioning and combinations can be configured adapted to optimize their operation for an intended application or environment. For example, without limitation, as shown in FIGS. 3A-3B an equal number of emitters and receivers may be provided. In alternate embodiments, an unequal number of emitters and receivers may be provided in various combinations.

Referring to FIGS. 2-3B, various embodiments having alternate configurations of optical sensors 16 are illustrated in connection with catheter 12. Each optical sensor 16 includes a receiver 32 and an emitter 34. In the illustrated embodiments, the optical sensors 16 are provided by a fiber optic cable 38, wherein sensors 16 are connected to peripheral wall 40 surrounding a lumen 42 disposed within body 18 of catheter 12. Lumen 42 is provided to carry various components for use in the catheter or contact assembly or provides a passageway for fluids, such as those needed for an irrigated electrode. FIG. 3A further illustrates three optical sensors 16 connected to the peripheral wall 40 in a paired configuration wherein receiver 32 and emitter 34 are provided adjacent to one another. Each optical sensor 16 may be positioned relative to one another circumferentially around peripheral wall 40 of lumen 42. In a particular embodiment, as generally shown in FIG. 3A, optical sensors 16 may be provided in the paired configuration, wherein the pairs are separated about peripheral wall 40 of fiber optic cable 38. Each of the pairs may be separated by various degrees, such as 120 degrees, as shown. FIG. 3B illustrates an example of an alternate embodiment, wherein a plurality of receivers 32 and emitters 34 are circumferentially disposed within the body of the catheter along the peripheral wall 40 from one another. Receivers 32 and emitters 34 may be provided in various combinations, ratios, and relative positions to one another depending on the design of the sensing assembly 10.

FIGS. 4-7 further illustrate an alternate embodiment of a contact sensing assembly 10. The assembly 10 includes catheter 12, electrode 14, and optical sensor 16, wherein distal end 20 of catheter 12 includes a coupling member 50 for receiving a portion of electrode 14 for connection with distal end 20 of catheter 12. The coupling member 50 includes a neck portion 52 and a mounting shaft 54.

Figure 5A:
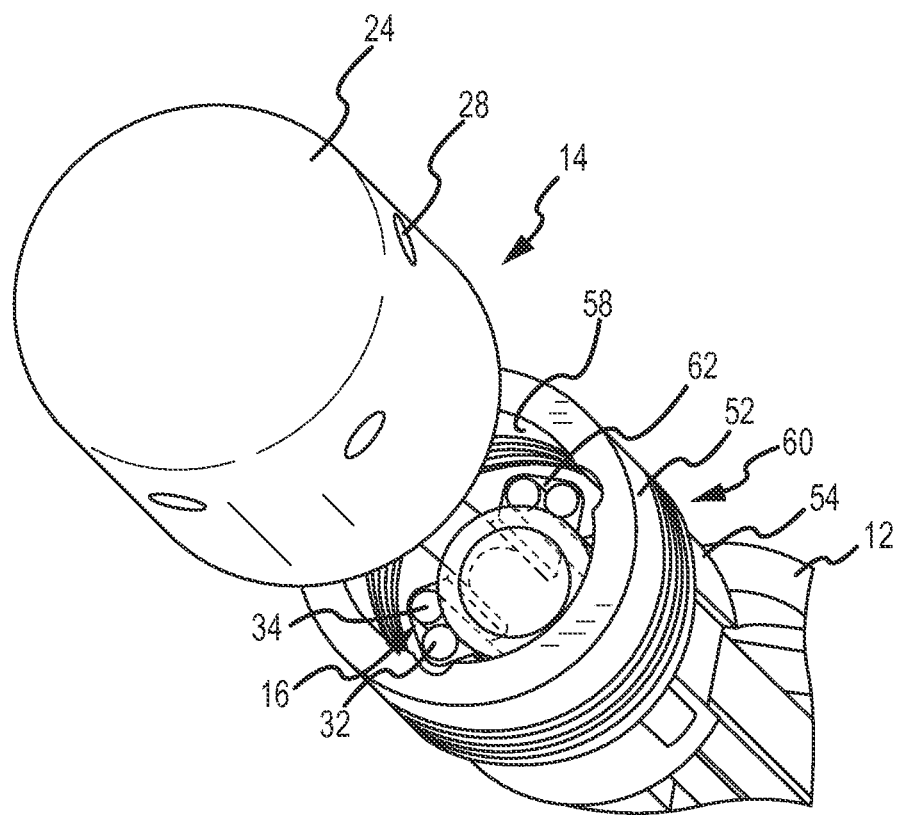
FIGS. 5A and 5B are exploded perspective views of an assembly of the type shown in FIG. 4.
Figure 5B:
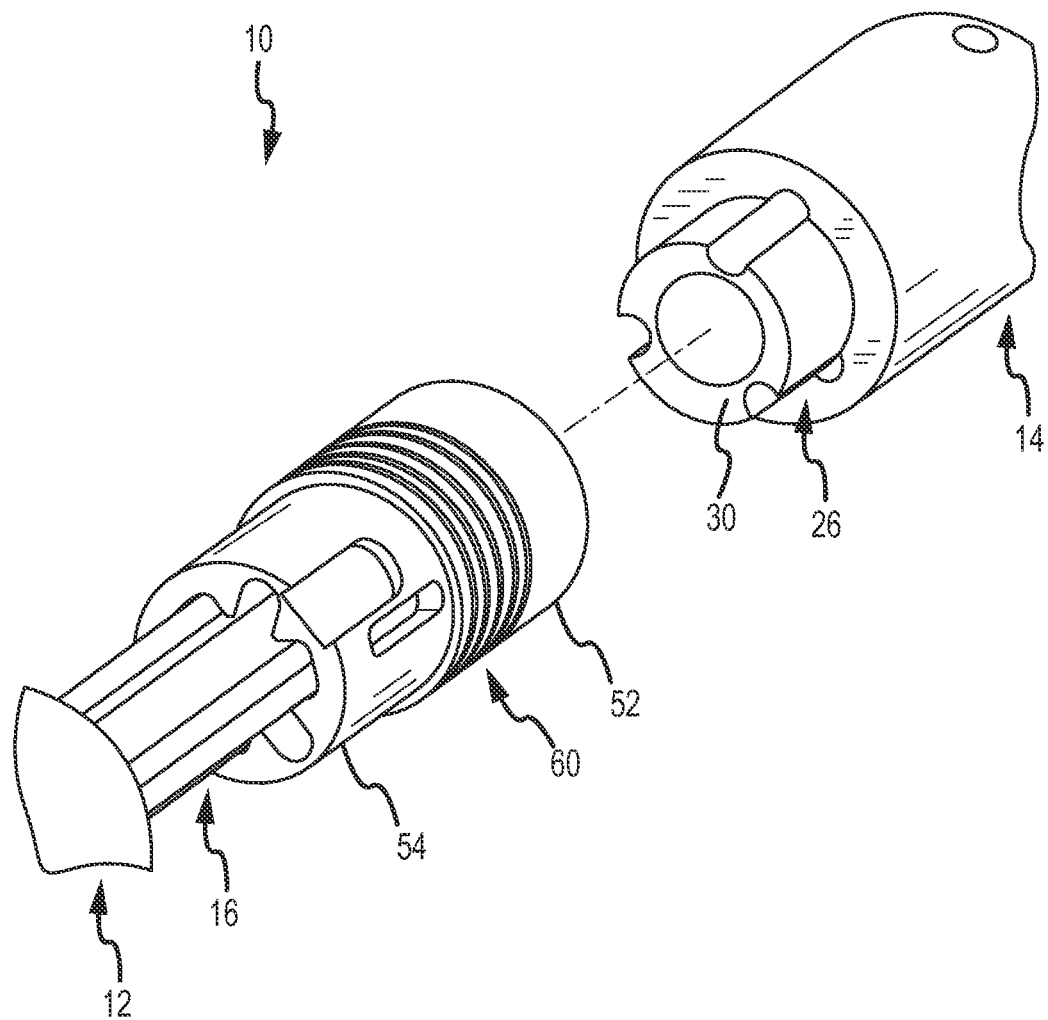

As shown in the combination of FIGS. 5A and 5B, the neck portion 52 of the coupling member 50 may define a receptacle of receiving portion 58 for receiving a portion of electrode 14 for connection with catheter 12. Base portion 26 of electrode 14 can be received by electrode receptacle or receiving portion 58 for connecting electrode 14 to coupling member 50. Neck portion 52 may further includes elastic portion 60, that provides increased flexibility. Elastic portion 60 may include a number of alternate embodiments, such as a spring. Elastic portion 60 of neck portion 52 moves relative to the external force exerted on tip portion 24 of electrode 14. Mounting shaft 54 of coupling member 50 is connected to catheter 12, therein forming a flexible distal end 20. In some embodiments, mounting shaft 54 is more rigid than neck portion 52 of coupling member 50 and provides secure engagement with catheter 12. At least one pull wire (not shown) may be attached to mounting shaft 54 for movement and deflection of the catheter. Mounting shaft 54 further provides at least one recessed groove 62 for receiving and mounting optical sensor 16. The recessed groove 62 may position optical sensor 16 so that the end of the optical sensor 16 is flush with mounting shaft 54. Alternate embodiments may provide for optical sensors that extend into the electrode. Overall, the optical sensors are positioned to interact with optically interactive surface 30 as provided by electrode 14. FIG. 5B provides an embodiment, wherein optically interactive surface 30 is provided on or is a part of base portion 26 of electrode 14. Optically interactive surface 30 may, in another embodiment, be provided as a coating or formed surface in connection with electrode 14.

Figure 9A:
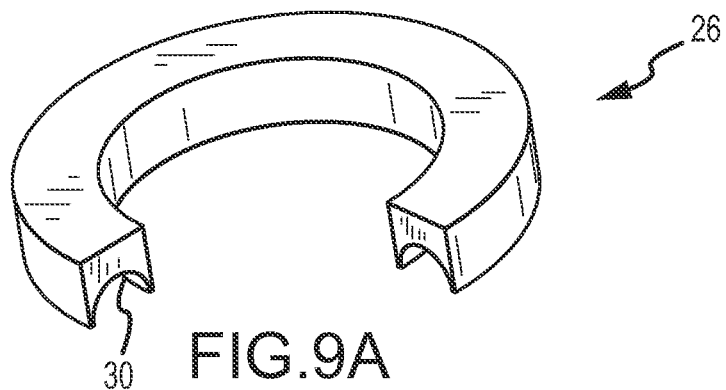
FIGS. 9A-9F are alternate embodiments of a portion of the assembly of the type shown in FIG. 5B.
Figure 9B:
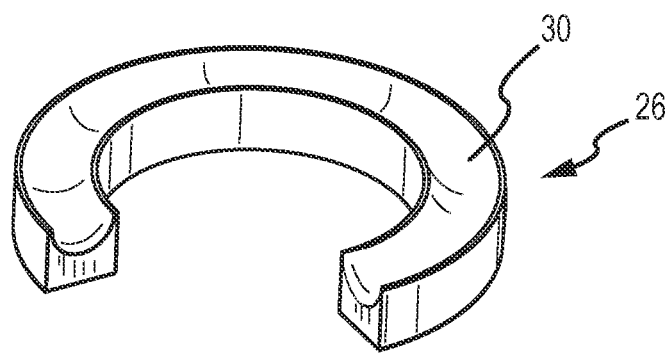
Figure 9C:
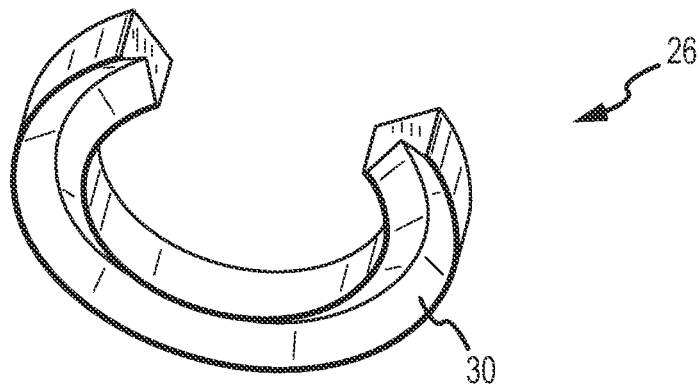
Figure 9D:
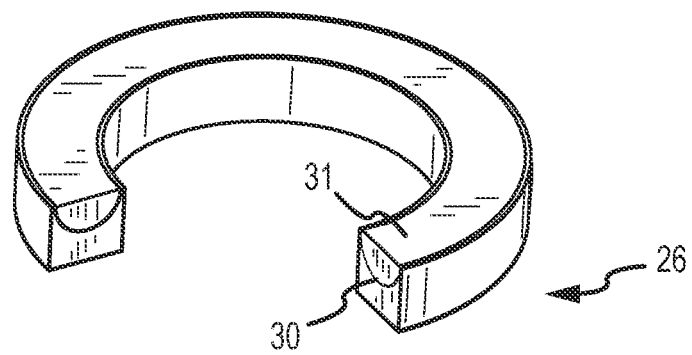
Figure 9E:
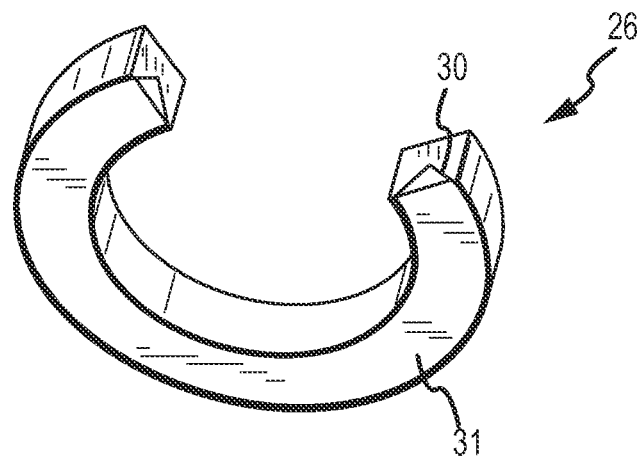
Figure 9F:
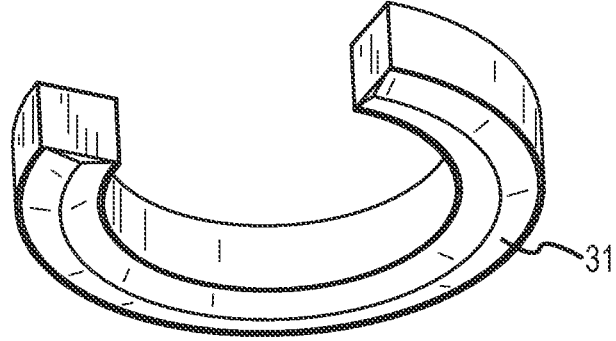

FIGS. 9A-9F generally illustrate alternate configurations of base portion 26 in accordance with alternate embodiments of the present invention. Although not shown, in the provided Figures, base portion 26 can be connected to and/or may be an integrated part of electrode 14, for example, as shown in FIG. 5B. FIGS. 9A-9C provide alternate embodiments of optically interactive surface 30 as provided by base portion 26, wherein optically interactive surface 30 may be hemispherical in shape or provided in a more angular/planar design. The design of optically interactive surface may vary depending on the physical requirements of the optical system and the desired interaction with the optical signal emitted and reflected by the associated optical sensor or sensors. In alternate embodiments, as shown in FIGS. 9D-9F, refractive media 31 may be further provided by base portion 26 to optically interact with the signal (i.e., light) generated by optical senor 16 of the present invention. The media may be prismastic or plano-convex. Moreover, optically interactive surface 30 may further be provided in connection with the media 31. Media 31 may further include various lens, filters or other types of structures generally know to interact with optical signals (i.e., light).

Figure 6:
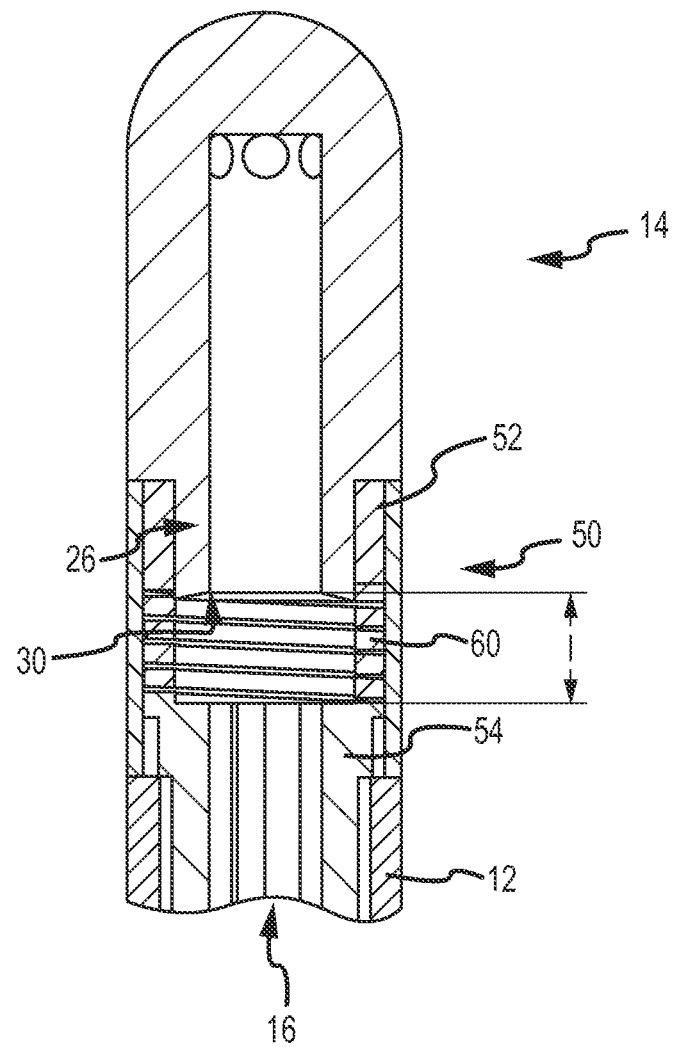
FIG. 6 is a side cross-sectional view of an assembly of the type shown in FIG. 4.
Figure 7:
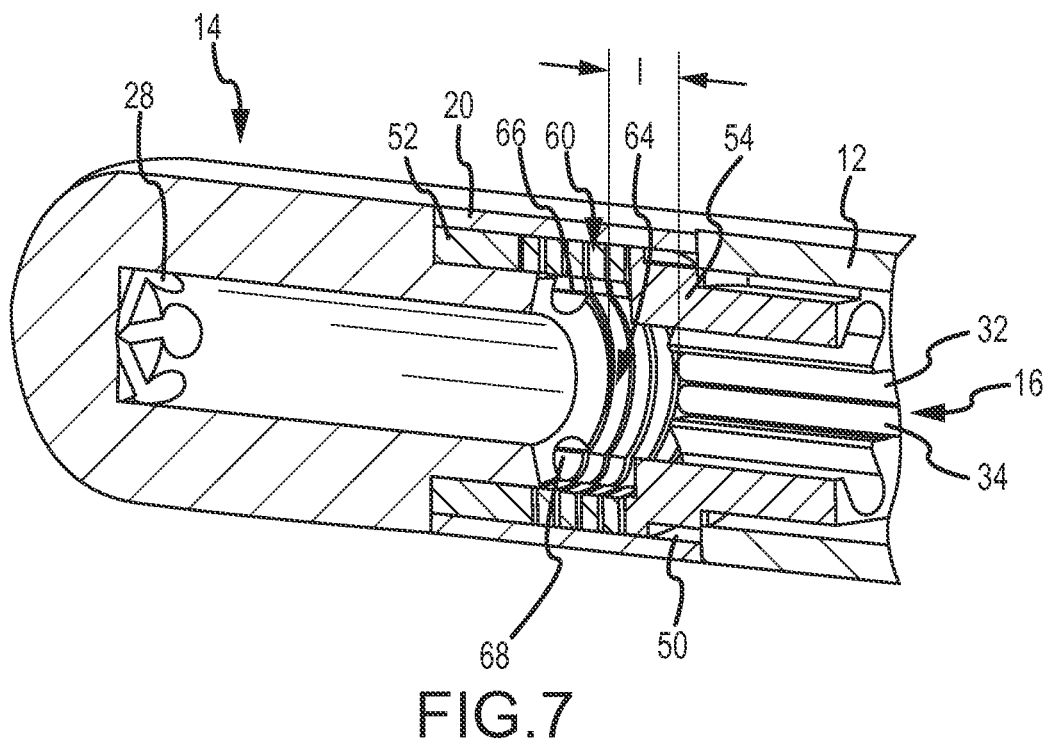
FIG. 7 is a side cross-sectional view of an assembly in accordance with another embodiment of the present invention.
Figure 8:
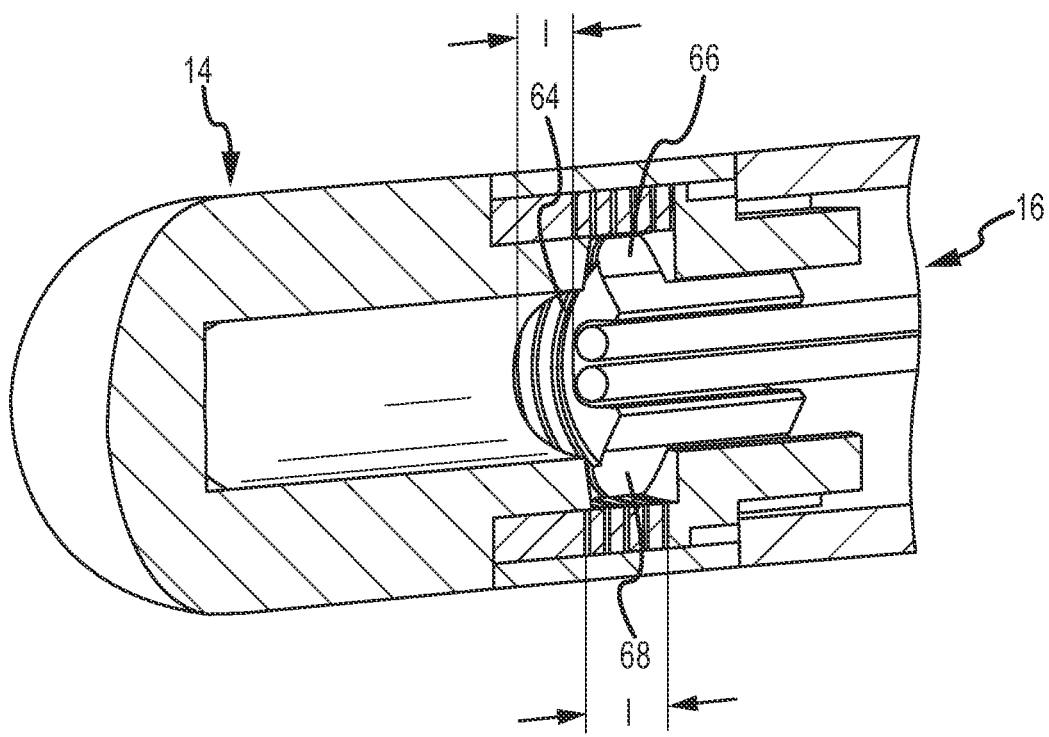
FIG. 8 is a cross-sectional view of an assembly in accordance with another embodiment of the present invention.

As generally illustrated in FIGS. 6-8, base portion 26 of electrode 14 is positioned within neck portion 52 of the coupling member 50 so that a gap and/or area 64 is provided between optical sensors 16 and optically interactive surface 30. As tip portion 24 of electrode 14 is exposed to external force through contact with tissue, neck portion 52 of coupling member 50 moves relative to tip 24 of electrode 14. Gap 64 may vary in size depending on the size of the electrode, as well as the desired optical interaction between the electrode and the optical sensor. The length (l) of gap 64 correlates to the size of elastic coupling 60 as provided by neck portion 54 of coupling member 50.

An alternate embodiment, the volume of the area generally defined by gap 64 may also be filled, in whole or in part, with a medium 33 that transmits/transfers light. Medium 33 may further allow for the optical interaction of optical sensor 16 with surface 30 associated with electrode 14. Accordingly, the optical signal emitted from optical sensor 16 may be transmitted either through medium 33 or may directly interact with optically interactive surface 30 depending on the position and/or orientation of catheter 12 and the design of the assembly. The interaction and orientation of the signal may be correlated to determine an associated amount of external force exerted on electrode 14 disposed on catheter 12, and may provide information concerning the orientation of the electrode 14. Moreover, the assembly may be calibrated to better ensure appropriate correlation. The optical signal is then reflected or refracted after interacting with optically interactive surface 30 and received by optical sensor 16. In an embodiment, the optical signal (e.g., light energy) is emitted by emitter 34 and received by receiver 32 of optical sensor 16.

Figure 10A:
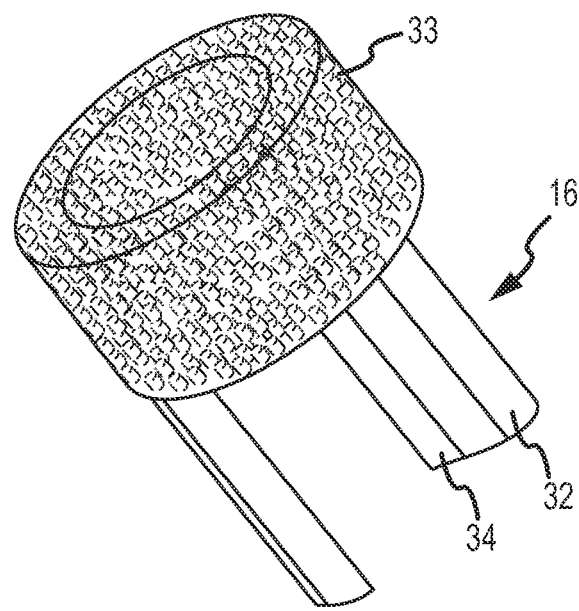
FIGS. 10A-10B are alternate embodiments of a portion of the assembly for incorporation with the present invention.
Figure 10B:
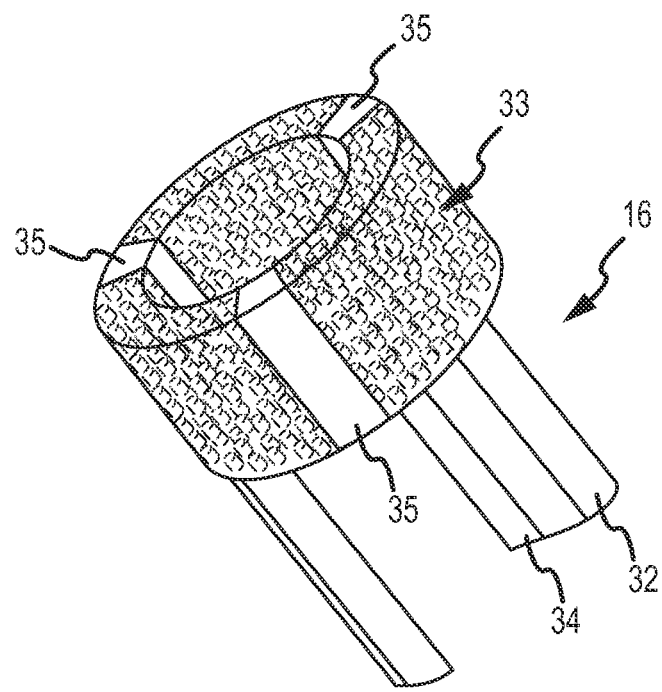

As can be seen in FIGS. 10A-10B, alternate configurations of medium 30 are shown. In particular, medium 33 may be positioned within the optical assembly such that the proximal surface of the medium 33 may be coupled to or in proximity with optical sensor 16, while the distal surface of medium 33 may be position in proximity to base portion 26 of electrode 14. Base portion 26 of electrode 14 may further include optically interactive surface 30. In an alternate configuration, medium 33 is provided to optically interact with the optical signal generated by optical sensor 16, in particular, emitter 34, therein refracting the optical signal for transmitting to receiver 32. Medium 33 may include air, gel, liquid or other types of compliant materials known in the industry that are suitable for the environment and do not unacceptably interfere with the operation of the electrode 14 or the optical sensor 16. In an embodiment, medium 33 may be encapsulated within a compliant retaining structure. Medium 33 may be compressible such that the material is responsive to external force as exerted on electrode 14. In an alternate embodiment, medium 33 may comprise a gel or liquid like material dispersed with a solid or solid particulate such that light is dispersed or refracted (i.e. scattered) by the particulate. An alternate embodiment may provide a liquid or gel-like material that further includes suspended particles (i.e. air or liquid bubbles) that would refract the optical signal provided by emitter 34 to receiver 32. FIG. 10B illustrates another embodiment, wherein opaque partitions 35 are positioned among medium 33, such that the optical signals emitted by each optical sensor 16 essentially cannot interfere with one another. Such a configuration can aid in reducing "cross-talk" and/or interference among each of the optical sensors 16.

A fiber assembly is further provided by the present invention. The fiber assembly includes a supply fiber and a return fiber. The supply fiber (not shown) is connected to emitter 34 and carries light energy from a light source to emitter 34. The return fiber (not shown) carries reflected light from receiver 32 back to a processor and display unit. The light energy emitted by optical sensor 16 is compared to the light received by optical sensor 16 and used to determine the relative force exerted on electrode 14 based on the orientation of electrode 14 and in connection with catheter 12.

In another embodiment, catheter assembly 10 provides a first interactive component and a second interactive component such the interactive components may include optical sensors, optically interactive surfaces in various combinations. For example, in an embodiment, that assembly does not necessarily include an electrode, but may provide a sensor that includes a segment with an interactive component and a tip with another interactive component adapted to interact with one another when an external surface of the tip contacts a target.

FIG. 7 illustrates an alternate embodiment of assembly 10 wherein least one lumen 66 is included for receiving various energizing or sensing components. Lumen 66 is provided for receiving sensing components such as a thermal sensor, pressure sensor, tissue sensor, electrogram sensor, or other type of sensors and combinations thereof that are known by those of ordinary skill in the art. An additional lumen 68 extends from catheter 12 through coupling member 50 and into electrode 14, therein providing an energizing component, such as source for radiofrequency current, direct current, high-intensity ultrasound, laser, cryogenics, or other type of energizing component and combinations that are known by those of ordinary skill in the art. Additional lumens may be provided by assembly 10 for communication with additional components for the assembly, such as electrical components, fluid (i.e. saline) passageways, or others known in the industry.

As can be seen in FIGS. 7 and 8, electrode 14 may have alternate tip configurations depending on the type of procedure or use of the catheter assembly. As previously suggested, electrode 14 may be provided having an irrigated electrode tip or a non-irrigated electrode tip. Each of these may be used in connection with embodiments of the present invention.

Figure 11A:
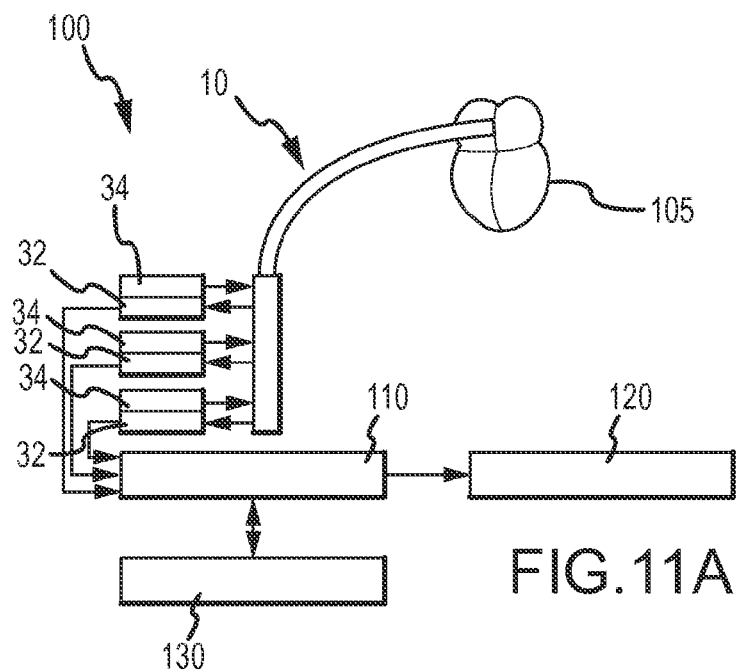
FIGS. 11A-11I are schematic overviews of the system in accordance with alternate embodiments of the present invention.
Figure 11B:
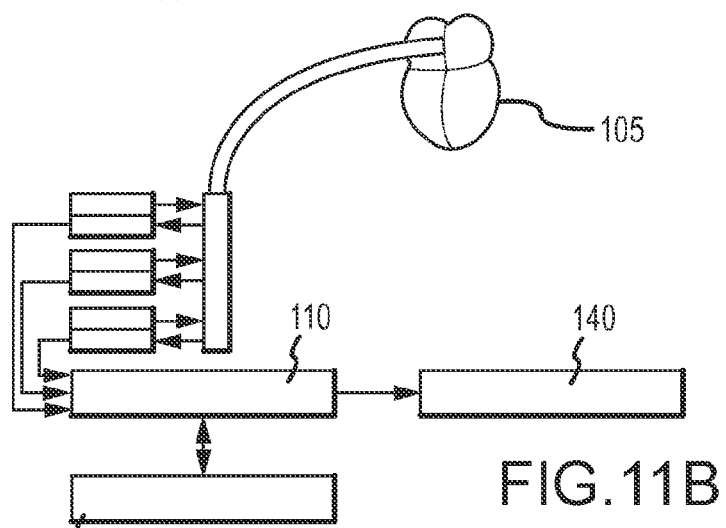
Figure 11C:
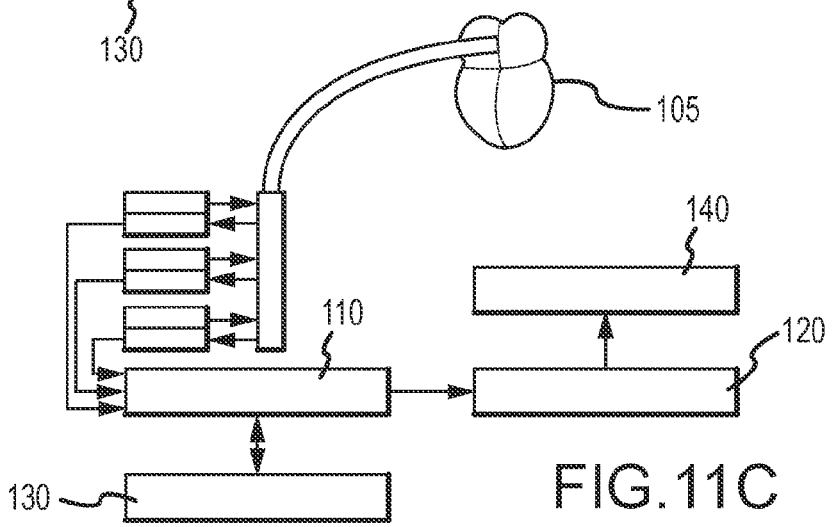
Figure 11D:
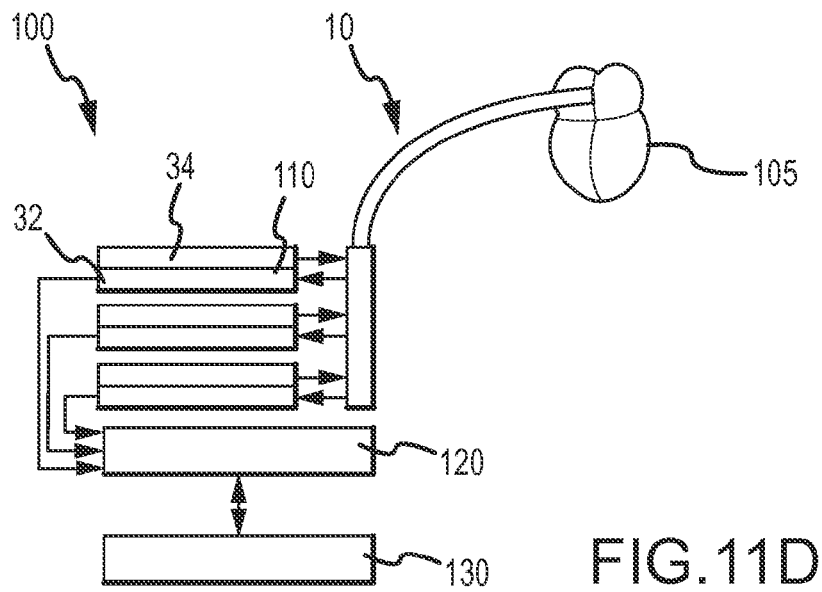
Figure 11E:
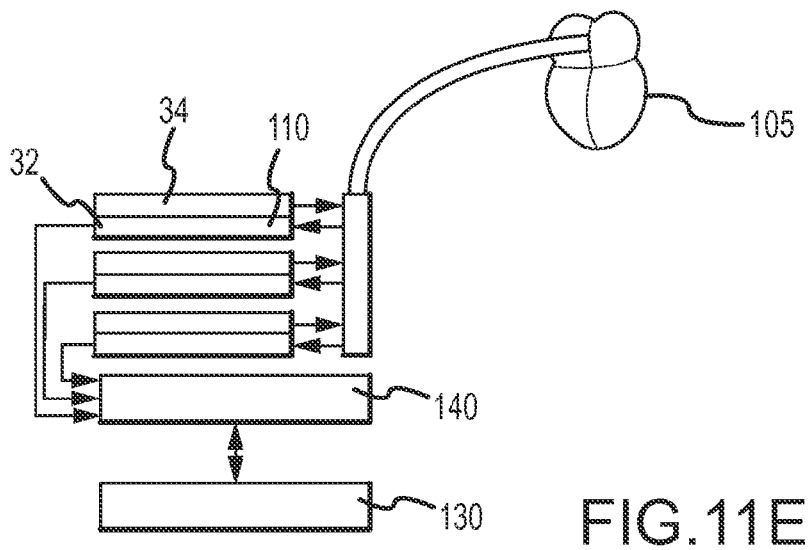
Figure 11F:
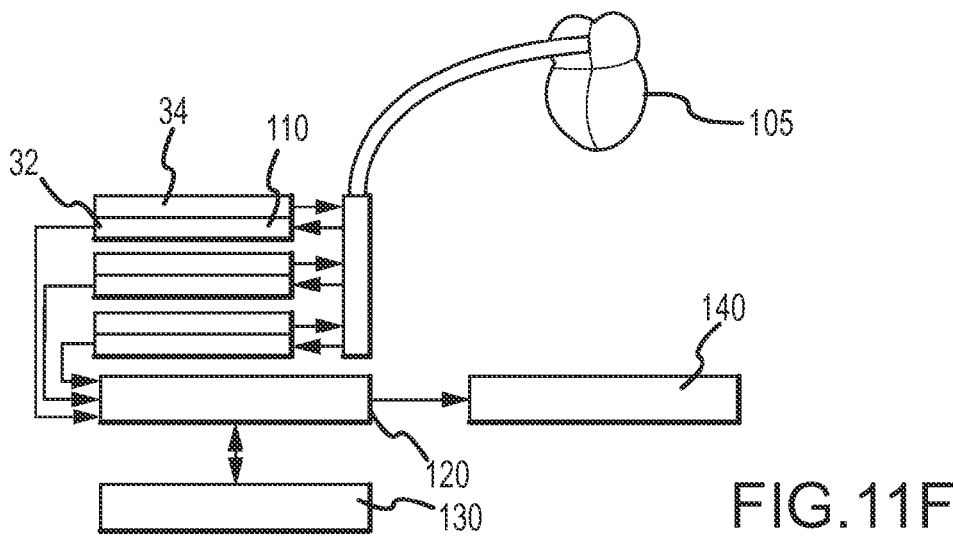
Figure 11G:
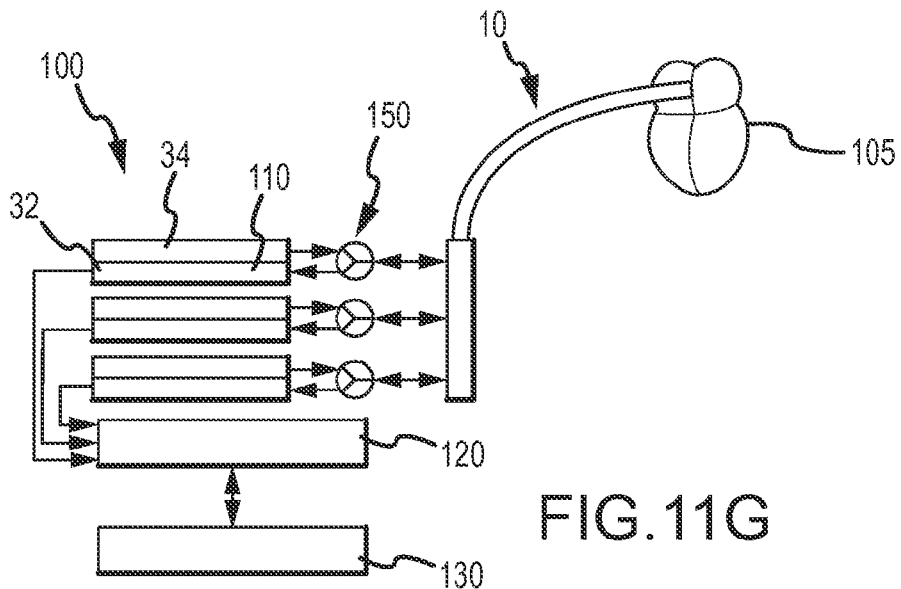
Figure 11H:
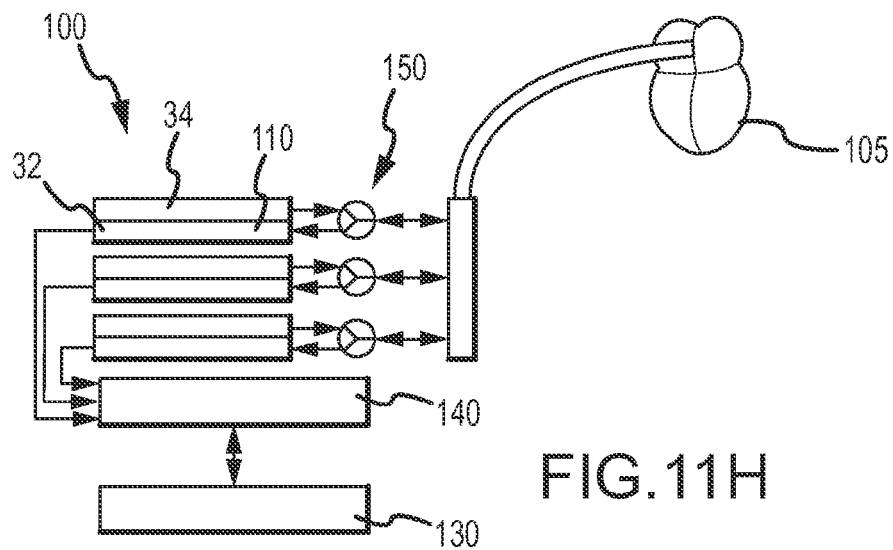
Figure 11I:
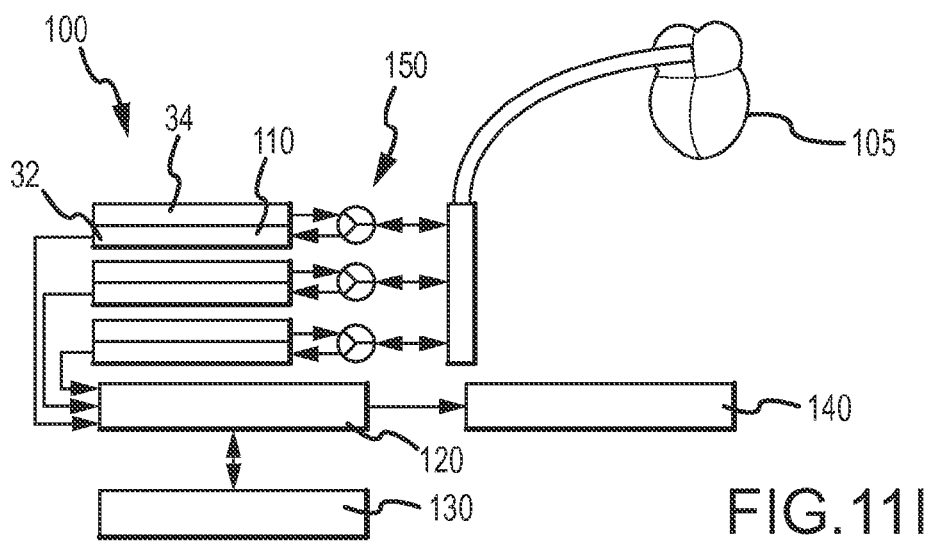

The present invention further discloses an optic-based catheter system 100, as shown in FIGS. 11A-11F, that includes assembly 10 of the present invention connected to a signal converter 110 (such as an analog to digital converter) and an operator interface 120, which may further include a computer and display, for processing the optical signals received from assembly 10 in connection with positioning and contact with tissue, such as myocardial tissue 105. This optic-based information is processed to determine the contact force exerted on electrode 14 of assembly 10. A calibration system 130 (i.e., calibration software) may be further provided to readily correlate the amplitude or intensity of the received signal to the external force on the electrode. A mapping system 140, such as the Ensite system, also known as NavX®, may be integrated with system 100 to provide a visualization and mapping system for use in connection with assembly 10 of the present invention. In an alternate embodiment, as shown in FIGS. 11D-11F, the signal processor may be integrated with each of the receivers provided by optical sensor 16, such that the optical signal is directly processed and provided on the operator interface. Moreover, in another alternate embodiment, as shown in FIGS. 11G-11I, the emitter and receiver may use the same optical fiber for transmitting and receiving the optical signal. Accordingly a splitter 150, as known by one of ordinary skill in the art, may be used to manage the transmission and receiving of the optical signal for processing. Overall, each of these components may be modified and/or integrated with one another depending on the design of the optical system as recognized by one of ordinary skill in the art.

As previously described, the present invention provides a method of sensing contact force and/or orientation as provided by the contact sensing assembly and system. The inventive method includes directing light or energy from a source through an optical sensor within a catheter; emitting light or energy from the optical sensor across a spaced gap for interacting with an optically-interactive surface provided in connection with an electrode; and receiving reflected light or energy by the optical sensor. The reflected light or energy may be processed by a processor to determine a change between the light or energy emitted from the optical sensor and the reflected light energy correspondingly received by the optical sensor. The changes may be correlated to, among other things, force vectors exerted by the electrode on a adjacent tissue.

In particular, under normal conditions of zero-contact force (i.e. when the electrode is not subjected to external forces), the plane of reflection as provided by either optically interactive surface 30, media 31 or medium 33, alone or in combination with one another as the case may be, is generally parallel to the plane of emitters 34 as previously described. Accordingly, the amplitude or intensity of the optical signal (i.e., light) received by receivers 32 is substantially the same or proportionally constant depending on the properties of the interactive surface. When the electrode contacts a surface, the contact force modifies the plane of reflection provided by the respective interactive surface (30, 31, or 33). In particular, upon the exertion of axial force ($F_a$) on the electrode, the plane of reflection is pushed closer to the place of emitters due to the spring-like configuration and/or flexibility exhibited by distal end 20 of catheter 12. Similarly, upon the exertion of lateral force ($F_l$), the place of reflection is tilted with respect to the plane of emitters. The change in amplitude or intensity of the reflected optical signal (i.e. light) received by each of the receivers relative to one another results in the calculation of the lateral force exerted on the external surface of the electrode. The change in amplitude or intensity of the reflected light relative to the zero-axial-force condition can be used to determine the axial force being exerted on the electrode. As a result, the net contact force is given by the vector sum of the axial and lateral force, and the direction relative to the axis may be calculated. Overall, the force, either axial, lateral or a combination of both, is determined based on the change of intensity of the optical signal received by the receivers which is proportional to the displacement and/or movement of the distal end 20 of catheter 12.

Although a number of embodiments of this invention have been described above with a certain degree of particularity, those skilled in the art could make numerous alterations to the disclosed embodiments without departing from the spirit or scope of this invention. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A contact sensing assembly comprising:
a catheter including a body defining an axis extending between a proximal end and a distal end;
an electrode including a tip portion and a base portion, the base portion configured to be received within the catheter body and to be movable along the axis relative to a portion of the catheter body; and
an optical sensor,
wherein the base portion of the electrode includes an optically interactive surface configured to reflect a signal from the optical sensor, the optically interactive surface being unitary with or rigidly coupled with the tip portion so as to move in unison with the tip portion; a portion of the electrode is connected to the distal end of the catheter; and the optical sensor is spaced from, operatively interacts with, and is moveable along the axis and radial to the axis relative to the optically interactive surface such that the relative intensity of the signal as reflected by the optically interactive surface is indicative of an external axial force and an external radial force applied to the electrode.

2. The assembly of claim 1 wherein the optical sensor is configured to send and receive light energy or a light-based signal.

3. The assembly of claim 1, wherein the distal end of the catheter includes a coupling member having a neck portion.

4. The assembly of claim 3, wherein the neck portion of the coupling member allows the base portion to move axially relative to the portion of the catheter body according to an external force exerted on the electrode.

5. The assembly of claim 3, including a mounting shaft that defines an internal recessed groove for receiving at least a portion of the optical sensor.

6. The assembly of claim 1, wherein the tip portion of the electrode includes an irrigation port.

7. The assembly of claim 1, wherein the electrode comprises a lumen provided within an internal cavity of the electrode, the lumen positioned adjacent to the base portion and tip portion of the electrode.

8. The assembly of claim 1, wherein the assembly further includes a refractive media or medium.

9. The assembly of claim 8, wherein the refractive media or medium includes a reflective surface.

10. The assembly of claim 1, wherein the optical sensor includes an emitter and a receiver.

11. The assembly of claim 10, wherein the emitter and receiver are provided within a single optic fiber.

12. The assembly of claim 10, wherein the emitter and receiver are adjacent to one another and are paired.

13. The assembly of claim 10, wherein a plurality of emitters and a plurality of receivers are distributed about the peripheral wall of a fiber optic cable, such that each emitter operatively interacts with at least one receiver.

14. The assembly of claim 1, wherein the optical sensor includes a fiber optic cable comprising at least one lumen and a peripheral wall surrounding the lumen, wherein the optical sensor is connected to the peripheral wall.

15. The assembly of claim 14, wherein a plurality of optical sensors are disposed within the body of the catheter, each optical sensor having an emitter for emitting light energy and a receiver for receiving light energy.

16. The assembly of claim 15, wherein the optical sensors are circumferentially disposed within the body of the catheter.

17. The assembly of claim 1, comprising a lumen disposed within the body of the catheter, at least a portion of the lumen extending into the electrode for slidably receiving at least one sensing component.

18. The assembly of claim 17, wherein the sensing component is selected from a thermal sensor, pressure sensor, tissue sensor, electrogram sensor, and combinations thereof.

19. The assembly of claim 1, comprising a lumen disposed within the body of the catheter, at least a portion of the lumen extending into the electrode for slidably receiving at least one energizing component.

20. The assembly of claim 19, wherein the energizing component is selected from a radiofrequency current, direct current, high-intensity ultrasound, laser, cryogenic, and combinations thereof.

21. The assembly of claim 1, wherein the tip portion of the electrode includes a portion configured to perform ablation.

22. A contact sensing assembly comprising:
a catheter including a body defining an axis extending between a proximal end and a distal end;
an electrically-conductive electrode including a tip portion and a base portion, the tip portion unitary with the base portion; and
a sensor comprising:
an emitter configured to project an electromagnetic signal into the base portion of the electrode; and
a receiver, disposed in one or more of the base portion of the electrode and the distal end of the catheter body, configured to receive the electromagnetic signal;
wherein the electrode is axially and radially movable relative to a portion of the catheter body such that an amplitude of the received signal is indicative of an axial external force and a radial external force applied to the electrode.

* * * * *